(12) United States Patent
Samaritani et al.

(10) Patent No.: US 7,731,948 B2
(45) Date of Patent: Jun. 8, 2010

(54) STABILIZED INTERFERON LIQUID FORMULATIONS

(75) Inventors: Fabrizio Samaritani, Rome (IT); Alessandra Del Rio, Rome (IT)

(73) Assignee: Ares Trading S.A., Aubonne (CH)

( * ) Notice: Subject to any disclaimer, the term of this patent is extended or adjusted under 35 U.S.C. 154(b) by 531 days.

(21) Appl. No.: 11/597,987

(22) PCT Filed: May 27, 2005

(86) PCT No.: PCT/EP2005/052414

§ 371 (c)(1),
(2), (4) Date: Nov. 30, 2006

(87) PCT Pub. No.: WO2005/117949

PCT Pub. Date: Dec. 15, 2005

(65) Prior Publication Data

US 2007/0292391 A1    Dec. 20, 2007

Related U.S. Application Data

(60) Provisional application No. 60/616,378, filed on Oct. 6, 2004.

(30) Foreign Application Priority Data

Jun. 1, 2004    (EP) ................................ 04076626

(51) Int. Cl.
*A61K 38/21* (2006.01)
(52) U.S. Cl. ................................... 424/85.6
(58) Field of Classification Search ...................... None
See application file for complete search history.

(56) References Cited

U.S. PATENT DOCUMENTS

| | | | |
|---|---|---|---|
| 4,469,228 A | 9/1984 | Zupon et al. | |
| 4,588,585 A | 5/1986 | Mark et al. | |
| 4,695,623 A | 9/1987 | Stabinsky | |
| 4,737,462 A | 4/1988 | Mark et al. | |
| 4,879,111 A | 11/1989 | Chong | |
| 4,897,471 A | 1/1990 | Stabinsky | |
| 4,904,584 A | 2/1990 | Shaw | |
| 4,959,314 A | 9/1990 | Mark et al. | |
| 4,965,195 A | 10/1990 | Namen et al. | |
| 5,017,691 A | 5/1991 | Lee et al. | |
| 5,116,943 A | 5/1992 | Koths et al. | |
| 5,541,293 A | 7/1996 | Stabinsky | |
| 5,762,923 A | 6/1998 | Gross et al. | |
| 5,858,001 A | 1/1999 | Tsals et al. | |
| 6,013,253 A | 1/2000 | Martin et al. | |
| 6,130,200 A | 10/2000 | Brodbeck et al. | |
| 6,531,122 B1 | 3/2003 | Pedersen et al. | |
| 6,569,420 B2 * | 5/2003 | Chen et al. | 424/85.4 |
| 6,852,314 B1 | 2/2005 | Samaritani et al. | |
| 6,923,956 B1 | 8/2005 | Tschope et al. | |
| 2002/0172661 A1 | 11/2002 | Shirley et al. | |
| 2003/0138491 A1 | 7/2003 | Tracy et al. | |
| 2007/0059285 A1 | 3/2007 | Samaritani et al. | |
| 2007/0092487 A1 | 4/2007 | Samaritani et al. | |
| 2007/0248674 A1 | 10/2007 | Del Curto et al. | |

FOREIGN PATENT DOCUMENTS

| | | |
|---|---|---|
| EP | 0098110 | 1/1984 |
| EP | 0177153 | 4/1986 |
| EP | 0509968 | 10/1992 |
| EP | 736303 | 10/1996 |
| EP | 1224940 A1 | 9/1998 |
| EP | 1250932 A1 | 5/2000 |
| WO | WO 95/31213 | 11/1995 |
| WO | WO 99/55377 A3 | 11/1999 |
| WO | WO 00/24374 | 5/2000 |
| WO | WO 01/03737 | 1/2001 |
| WO | WO 01/58474 | 8/2001 |
| WO | WO 02/03472 | 1/2002 |
| WO | WO 02/09766 | 2/2002 |
| WO | WO 02/051386 | 7/2002 |
| WO | WO 03/066585 | 8/2003 |
| WO | WO 2004/002404 | 1/2004 |
| WO | WO 2005/110466 | 11/2005 |

OTHER PUBLICATIONS

Cook, S. D. "Advancing Treatment with Interferon beta-1b (Betaferone®/Betaseron®) in the Next Decade", *J. Neurol.*, 2003, pp. IV/15-IV/20, vol. 25, Suppl. 4.
Derynck, R. et al. "Isolation and Structure of a Human Fibroblast Interferon Gene", *Nature*, Jun. 19, 1980, pp. 542-547, vol. 285.
Rubinstein, S. et al. "Convenient Assay for Interferons", *Journal of Virology*, Feb. 1981, pp. 755-758, vol. 37, No. 2.
Familletti, P. C. et al. "A Convenient and Rapid Cytopathic Effect Inhibition Assay for Interferon", *Methods in Enzymology*, 1981, pp. 387-394, vol. 78.
Shepard, H. M. et al. "A Single Amino Acid Change in IFN-$\beta_1$ Abolishes its Antiviral Activity", *Nature*, Dec. 10, 1981, pp. 563-565, vol. 294.
Mark, D. F. et al. "Site-Specific Mutagenesis of the Human Fibroblast Interferon Gene", *Proc. Natl. Acad. Sci.*, Sep. 1984, pp. 5662-5666, vol. 81.
Pestka, S. "Interferon Standards and General Abbreviations", *Methods in Enzymology*, 1986, pp. 14-23, vol. 119.
Lam, X. M. et al. "The Effect of Benzyl Alcohol on Recombinant Human Interferon-γ", *Pharmaceutical Research*, 1997, pp. 725-729, vol. 14, No. 6.
Schuck, P. "Size-Distribution Analysis of Macromolecules by Sedimentation Velocity Ultracentrifugation and Lamm Equation Modeling", *Biophysical Journal*, Mar. 2000, pp. 1606-1619, vol. 78.
Wang, W. "Instability, Stabilization, and Formulation of Liquid Protein Pharmaceuticals", *International Journal of Pharmaceutics*, 1999, pp. 129-188, vol. 185.

(Continued)

*Primary Examiner*—Robert Landsman
(74) *Attorney, Agent, or Firm*—Saliwanchik, Lloyd & Saliwanchik

(57) ABSTRACT

A stabilized HSA-free liquid pharmaceutical composition is described, which comprises an interferon (IFN), wherein said formulation is a solution that comprises a buffer, an amino acid and an antioxidant. Preferably, the interferon is human recombinant IFN-beta.

2 Claims, No Drawings

OTHER PUBLICATIONS

Wang, Y.-C. J. et al. "Parenteral Formulations of Proteins and Peptides: Stability and Stabilizers", *Journal of Parenteral Science & Technology*, 1988, pp. S4-S26, vol. 42.

Bromberg, L. E. et al. "Temperature-responsive Gels and Thermogelling Polymer Matrices for Protein and Peptide Delivery", *Advanced Drug Delivery Reviews*, 1998, pp. 197-221, vol. 31.

Chen-Chow, P.-C. et al. "In Vitro Release of Lidocaine from Pluronic F-127 Gels", *International Journal of Pharmaceutics*, 1981, pp. 89-99, vol. 8.

Gander, B. et al. "Crosslinked Poloxamers as a Versatile Monolithic Drug Delivery System", *Drug Devel. And Indust. Pharmacy*, 1986, pp. 1613-1623, vol. 12, Nos. 11-13.

Guzmán, M. et al. "Polyoxyethylene-polyoxypropylene Block Copolymer Gels as Sustained Release Vehicles for Subcutaneous Drug Administration", *International Journal of Pharmaceutics*, 1992, pp. 119-127, vol. 80.

Johnston, T. P. et al. "Sustained Delivery of Interleukin-2 from a Poloxamer 407 Gel Matrix Following Intraperitoneal Injection in Mice", *Pharmaceutical Research*, 1992, pp. 425-434, vol. 9, No. 3.

Katakam, M. et al. "Controlled Release of Human Growth Hormone in Rats Following Parenteral Administration of Poloxamer Gels", *Journal of Controlled Release*, 1997, pp. 21-26, vol. 49.

Miyazaki, S. et al. "Pluronic F-127 Gels as a Novel Vehicle for Rectal Administration of Indomethacin", *Chem. Pharm. Bull.*, 1986, pp. 1801-1808, vol. 34, No. 4.

Schmolka, I. R. "A Review of Block Polymer Surfactants", *Journal of the American Oil Chemists' Society*, Mar. 1977, pp. 110-116, vol. 54.

Stewart, W. E. et al. "Interferon Nomenclature", *J. Interferon Res.*, 1980, pp. vi-vii, vol. 1.

Stratton, L. P. et al. "Drug Delivery Matrix Containing Native Protein Precipitates Suspended in a Poloxamer Gel", *Journal of Pharmaceutical Sciences*, Sep. 1997, pp. 1006-1010, vol. 86, No. 9.

Database WPI, Section Ch, Week 200406, Derwent Publicatons, Ltd., AN 2004-056676, XP-002301962 "Formulation for Injection of Interferon, Contains Interferon-alpha and Polyoxyethylene Polyoxypropylene Glycol", Dec. 3, 2003, 1 page.

Prisms Study Group "Randomised double-blind placebo-controlled study of interferon β-1a in relapsing/remitting multiple sclerosis" *The Lancet*, Nov. 7, 1998, pp. 1498-1504, vol. 352.

Clegg, A. et al. "Immunomodulatory drugs for multiple sclerosis: a systematic review of clinical and cost effectiveness" *Exp. Opin. Pharmacother.*, 2001, pp. 623-639, vol. 2, No. 4.

Hultgren, C. et al. "The antiviral compound ribavirin modulates the T helper (Th)1/Th2 subset balance in hepatitis B and C virus-specific immune responses" *Journal of General Virology*, 1998, pp. 2381-2391, vol. 79.

McCormick, J. B. et al. "Lassa Fever effective therapy with ribavirin" *The New England Journal of Medicine*, Jan. 2, 1986, pp. 20-26, vol. 314, No. 1.

Office Action dated Apr. 2, 2009 in U.S. Appl. No. 10/554,602.

Office Action dated Mar. 23, 2009 in U.S. Appl. No. 11/596,599.

Polman, C.H. et al. "Drug Treatment of Multiple Sclerosis" *BMJ*, Aug. 19-26, 2000, pp. 490-494, vol. 321.

* cited by examiner

STABILIZED INTERFERON LIQUID FORMULATIONS

CROSS-REFERENCE TO RELATED APPLICATION

This application is the U.S. national stage application of International Patent Application No. PCT/EP2005/052414, filed May 27, 2005, which claims the benefit of U.S. Provisional Patent Application No. 60/616,378, filed Oct. 6, 2004, the disclosures of which are hereby incorporated by reference in their entireties, including all figures, tables and amino acid or nucleic acid sequences.

FIELD OF THE INVENTION

The invention relates to HSA-free pharmaceutical compositions containing an interferon, more particularly to formulations of interferon-beta comprising a buffer, an amino acid and an antioxidant.

BACKGROUND OF THE INVENTION

Interferons are cytokines, i.e. soluble proteins that transmit messages between cells and play an essential role in the immune system by helping to destroy microorganisms that cause infection and repairing any resulting damage. Interferons are naturally secreted by infected cells and were first identified in 1957. Their name is derived from the fact that they "interfere" with viral replication and production.

Interferons exhibit both antiviral and antiproliferative activity. On the basis of biochemical and immunological properties, the naturally-occurring human interferons are grouped into three major classes: interferon-alpha (leukocyte), interferon-beta (fibroblast) and interferon-gamma (immune). Alpha-interferon is currently approved in the United States and other countries for the treatment of hairy cell leukemia, venereal warts, Kaposi's Sarcoma (a cancer commonly afflicting patients suffering from Acquired Immune Deficiency Syndrome (AIDS)), and chronic non-A, non-B hepatitis.

Further, interferons (IFNs) are glycoproteins produced by the body in response to a viral infection. They inhibit the multiplication of viruses in protected cells. Consisting of a lower molecular weight protein, IFNs are remarkably non-specific in their action, i.e. IFN induced by one virus is effective against a broad range of other viruses. They are however species-specific, i.e. IFN produced by one species will only stimulate antiviral activity in cells of the same or a closely related species. IFNs were the first group of cytokines to be exploited for their potential anti-tumor and antiviral activities.

The three major IFNs are referred to as IFN-α, IFN-β and IFN-γ. Such main kinds of IFNs were initially classified according to their cells of origin (leukocyte, fibroblast or T cell). However, it became clear that several types might be produced by one cell. Hence leukocyte IFN is now called IFN-α, fibroblast IFN is IFN-β and T cell IFN is IFN-γ. There is also a fourth type of IFN, lymphoblastoid IFN, produced in the "Namalwa" cell line (derived from Burkitt's lymphoma), which seems to produce a mixture of both leukocyte and fibroblast IFN.

The interferon unit or International unit for interferon (U or IU, for international unit) has been reported as a measure of IFN activity defined as the amount necessary to protect 50% of the cells against viral damage. The assay that may be used to measure bioactivity is the cytopathic effect inhibition assay as described (Rubinstein, et al. 1981; Familletti, P. C., et al., 1981). In this antiviral assay for interferon about 1 unit/ml of interferon is the quantity necessary to produce a cytopathic effect of 50%. The units are determined with respect to the international reference standard for Hu-IFN-beta provided by the National Institutes of Health (Pestka, S. 1986).

Every class of IFN contains several distinct types. IFN-β and IFN-γ are each the product of a single gene.

The proteins classified as IFNs-α are the most diverse group, containing about 15 types. There is a cluster of IFN-α genes on chromosome 9, containing at least 23 members, of which 15 are active and transcribed. Mature IFNs-α are not glycosylated.

IFNs-α and IFN-β are all the same length (165 or 166 amino acids) with similar biological activities. IFNs-γ are 146 amino acids in length, and resemble the α and β classes less closely. Only IFNs-γ can activate macrophages or induce the maturation of killer T cells. These new types of therapeutic agents can are sometimes called biologic response modifiers (BRMs), because they have an effect on the response of the organism to the tumor, affecting recognition via immunomodulation.

Human fibroblast interferon (IFN-β) has antiviral activity and can also stimulate natural killer cells against neoplastic cells. It is a polypeptide of about 20,000 Da induced by viruses and double-stranded RNAs. From the nucleotide sequence of the gene for fibroblast interferon, cloned by recombinant DNA technology, (Derynk et al. 1980) deduced the complete amino acid sequence of the protein. It is 166 amino acid long.

Shepard et al. (1981) described a mutation at base 842 (Cys→Tyr at position 141) that abolished its anti-viral activity, and a variant clone with a deletion of nucleotides 1119-1121.

Mark et al. (1984) inserted an artificial mutation by replacing base 469 (T) with (A) causing an amino acid switch from Cys→Ser at position 17. The resulting IFN-β was reported to be as active as the 'native' IFN-β and stable during long-term storage (−70° C.).

REBIF (Serono—recombinant human interferon-β), the latest development in interferon therapy for multiple sclerosis (MS), is interferon (IFN)-beta-1a, produced from mammalian cell lines. Its recommended International Non-proprietary Name (INN) is "Interferon beta-1a".

As with all protein-based pharmaceuticals, one major obstacle that must be overcome in the use of IFN-.beta. as a therapeutic agent, is the loss of pharmaceutical utility that can result from its instability in pharmaceutical formulations.

Physical instabilities that threaten polypeptide activity and efficacy in pharmaceutical formulations include denaturation and formation of soluble and insoluble aggregates, while chemical instabilities include hydrolysis, imide formation, oxidation, racemization, and deamidation. Some of these changes are known to lead to the loss or reduction of the pharmaceutical activity of the protein of interest. In other cases, the precise effects of these changes are unknown, but the resulting degradative products are still considered to be pharmaceutically unacceptable due to the potential for undesirable side effects.

The stabilization of polypeptides in pharmaceutical compositions remains an area in which trial and error plays a major role (reviewed by Wang (1999) Int. J. Pharm. 185:129-188; Wang and Hanson (1988) J. Parenteral Sci. Tech. 42:S3-S26). Excipients that are added to polypeptide pharmaceutical formulations to increase their stability include buffers, sugars, surfactants, amino acids, polyethylene glycols, and polymers, but the stabilizing effects of these chemical additives vary depending on the protein.

In US 2002/0172661, IFN beta formulations are described that are characterized by their low ionic strength and a pH of about 3.0-5.0.

Current IFN-beta formulations employ the use of HSA as a solubility-enhancing agent for IFN-beta. However, the use of HSA has some drawbacks. HSA is a product of human blood and must therefore be harvested from human subjects. While steps are taken to reduce the risk, the use of human blood products such as HSA carries with it the potential introduction of human viruses such as HIV and HCV.

Consequently, there is a need for additional IFN-beta pharmaceutical compositions comprising physiologically compatible stabilizers that improve the solubility of this protein and stabilize the protein against aggregate formation, thereby enhancing their pharmaceutical utility.

DESCRIPTION OF THE INVENTION

The present invention is directed to stabilized pharmaceutical compositions that comprise an interferon (IFN) and methods for their preparation. These compositions are prepared in the absence of human serum albumin (HSA). Such compositions are referred to herein as "HSA-free". IFN HSA-free pharmaceutical compositions comprise an interferon (IFN) or an isoform, mutein, fused protein, functional derivative, active fraction or salt thereof, wherein said composition is a solution that comprises a buffer, an amino acid and an antioxidant.

According to an embodiment of the present invention the compositions also comprise a bacteriostatic agent.

An "interferon" or "IFN", as used herein, is intended to include any molecule defined as such in the literature, comprising for example any types of IFNs mentioned in the above section "Background of the Invention". In particular, IFN-α, IFN-β and IFN-γ are included in the above definition. IFN-β is the preferred IFN according to the present invention. IFN-β suitable in accordance with the present invention is commercially available e.g. as REBIF (Serono), AVONEX (Biogen) or BETAFERON (Schering). The use of interferons of human origin is also preferred in accordance with the present invention. The term interferon, as used herein, is intended to encompass an isoform, a mutein, a fused protein, a functional derivative, an active fraction or a salt thereof.

The term "interferon-beta (IFN-beta or IFN-β)", as used herein, is intended to include fibroblast interferon in particular of human origin, as obtained by isolation from biological fluids or as obtained by DNA recombinant techniques from prokaryotic or eukaryotic host cells, as well as its salts, functional derivatives, variants, analogs and active fragments. Preferably IFN-beta is intended to mean Interferon beta-1a.

As used herein the term "muteins" refers to analogs of IFN in which one or more of the amino acid residues of a natural IFN are replaced by different amino acid residues, or are deleted, or one or more amino acid residues are added to the natural sequence of IFN, without changing considerably the activity of the resulting products as compared to the wild type IFN. These muteins are prepared by known synthesis and/or by site-directed mutagenesis techniques, or any other known technique suitable therefore. Preferred muteins include e.g. the ones described by Shepard et al. (1981) or Mark et al. (1984).

Any such mutein preferably has a sequence of amino acids sufficiently duplicative of that of IFN, such as to have substantially similar or even better activity to an IFN. The biological function of interferon is well known to the person skilled in the art, and biological standards are established and available e.g. from the National Institute for Biological Standards and Control (http://immunology.org/links/NIBSC).

Bioassays for the determination of IFN activity have been described. An IFN assay may for example be carried out as described by Rubinstein et al., 1981. Thus, it can be determined whether any given mutein has substantially a similar, or even a better, activity than IFN by means of routine experimentation.

Muteins of IFN, which can be used in accordance with the present invention, or nucleic acid coding therefor, include a finite set of substantially corresponding sequences as substitution peptides or polynucleotides which can be routinely obtained by one of ordinary skill in the art, without undue experimentation, based on the teachings and guidance presented herein.

Preferred changes for muteins in accordance with the present invention are what are known as "conservative" substitutions. Conservative amino acid substitutions of polypeptides or proteins of the invention, may include synonymous amino acids within a group, which have sufficiently similar physicochemical properties that substitution between members of the group will preserve the biological function of the molecule. It is clear that insertions and deletions of amino acids may also be made in the above-defined sequences without altering their function, particularly if the insertions or deletions only involve a few amino acids, e.g., under thirty, and preferably under ten, and do not remove or displace amino acids which are critical to a functional conformation, e.g., cysteine residues. Proteins and muteins produced by such deletions and/or insertions come within the purview of the present invention.

Preferably, the synonymous amino acid groups are those defined in Table I. More preferably, the synonymous amino acid groups are those defined in Table II; and most preferably the synonymous amino acid groups are those defined in Table III.

TABLE I

Preferred Groups of Synonymous Amino Acids

| Amino Acid | Synonymous Group |
|---|---|
| Ser | Ser, Thr, Gly, Asn |
| Arg | Arg, Gln, Lys, Glu, His |
| Leu | Ile, Phe, Tyr, Met, Val, Leu |
| Pro | Gly, Ala, Thr, Pro |
| Thr | Pro, Ser, Ala, Gly, His, Gln, Thr |
| Ala | Gly, Thr, Pro, Ala |
| Val | Met, Tyr, Phe, Ile, Leu, Val |
| Gly | Ala, Thr, Pro, Ser, Gly |
| Ile | Met, Tyr, Phe, Val, Leu, Ile |
| Phe | Trp, Met, Tyr, Ile, Val, Leu, Phe |
| Tyr | Trp, Met, Phe, Ile, Val, Leu, Tyr |
| Cys | Ser, Thr, Cys |
| His | Glu, Lys, Gln, Thr, Arg, His |
| Gln | Glu, Lys, Asn, His, Thr, Arg, Gln |
| Asn | Gln, Asp, Ser, Asn |
| Lys | Glu, Gln, His, Arg, Lys |
| Asp | Glu, Asn, Asp |
| Glu | Asp, Lys, Asn, Gln, His, Arg, Glu |

TABLE I-continued

Preferred Groups of Synonymous Amino Acids

| Amino Acid | Synonymous Group |
|---|---|
| Met | Phe, Ile, Val, Leu, Met |
| Trp | Trp |

TABLE II

More Preferred Groups of Synonymous Amino Acids

| Amino Acid | Synonymous Group |
|---|---|
| Ser | Ser |
| Arg | His, Lys, Arg |
| Leu | Leu, Ile, Phe, Met |
| Pro | Ala, Pro |
| Thr | Thr |
| Ala | Pro, Ala |
| Val | Val, Met, Ile |
| Gly | Gly |
| Ile | Ile, Met, Phe, Val, Leu |
| Phe | Met, Tyr, Ile, Leu, Phe |
| Tyr | Phe, Tyr |
| Cys | Cys, Ser |
| His | His, Gln, Arg |
| Gln | Glu, Gln, His |
| Asn | Asp, Asn |
| Lys | Lys, Arg |
| Asp | Asp, Asn |
| Glu | Glu, Gln |
| Met | Met, Phe, Ile, Val, Leu |
| Trp | Trp |

TABLE III

Most Preferred Groups of Synonymous Amino Acids

| Amino Acid | Synonymous Group |
|---|---|
| Ser | Ser |
| Arg | Arg |
| Leu | Leu, Ile, Met |
| Pro | Pro |
| Thr | Thr |
| Ala | Ala |
| Val | Val |
| Gly | Gly |
| Ile | Ile, Met, Leu |
| Phe | Phe |
| Tyr | Tyr |
| Cys | Cys, Ser |
| His | His |
| Gln | Gln |
| Asn | Asn |
| Lys | Lys |
| Asp | Asp |
| Glu | Glu |
| Met | Met, Ile, Leu |
| Trp | Met |

Examples of production of amino acid substitutions in proteins which can be used for obtaining muteins of IFN, for use in the present invention include any known method steps, such as presented in U.S. Pat. Nos. 4,959,314, 4,588,585 and 4,737,462, to Mark et al; U.S. Pat. No. 5,116,943 to Koths et al., U.S. Pat. No. 4,965,195 to Namen et al; U.S. Pat. No. 4,879,111 to Chong et al; and U.S. Pat. No. 5,017,691 to Lee et al; and lysine substituted proteins presented in U.S. Pat. No. 4,904,584 (Shaw et al). Specific muteins of IFN-beta have been described, for example by Mark et al., 1984.

The term "fused protein" refers to a polypeptide comprising an IFN, or a mutein thereof, fused to another protein, which e.g., has an extended residence time in body fluids. An IFN may thus be fused to another protein, polypeptide or the like, e.g., an immunoglobulin or a fragment thereof.

"Functional derivatives" as used herein cover derivatives of IFN, and their muteins and fused proteins, which may be prepared from the functional groups which occur as side chains on the residues or the N- or C-terminal groups, by means known in the art, and are included in the invention as long as they remain pharmaceutically acceptable, i.e. they do not destroy the activity of the protein which is substantially similar to the activity IFN, and do not confer toxic properties on compositions containing it. These derivatives may, for example, include polyethylene glycol side-chains, which may mask antigenic sites and extend the residence of IFN in body fluids. Other derivatives include aliphatic esters of the carboxyl groups, amides of the carboxyl groups by reaction with ammonia or with primary or secondary amines, N-acyl derivatives of free amino groups of the amino acid residues formed with acyl moieties (e.g. alkanoyl or carbocyclic aroyl groups) or O-acyl derivatives of free hydroxyl groups (for example that of seryl or threonyl residues) formed with acyl moieties.

As "active fractions" of IFN, or muteins and fused proteins, the present invention covers any fragment or precursors of the polypeptide chain of the protein molecule alone or together with associated molecules or residues linked thereto, e.g., sugar or phosphate residues, or aggregates of the protein molecule or the sugar residues by themselves, provided said fraction has no significantly reduced activity as compared to the corresponding IFN.

The term "salts" herein refers to both salts of carboxyl groups and to acid addition salts of amino groups of the proteins described above or analogs thereof. Salts of a carboxyl group may be formed by means known in the art and include inorganic salts, for example, sodium, calcium, ammonium, ferric or zinc salts, and the like, and salts with organic bases as those formed, for example, with amines, such as triethanolamine, arginine or lysine, piperidine, procaine and the like. Acid addition salts include, for example, salts with mineral acids, such as, for example, hydrochloric acid or sulfuric acid, and salts with organic acids, such as, for example, acetic acid or oxalic acid. Of course, any such salts must retain the biological activity of the proteins (IFN) relevant to the present invention, i.e., the ability to bind to the corresponding receptor and initiate receptor signaling.

In accordance with the present invention, the use of recombinant human IFN-beta and the compounds of the invention is further particularly preferred.

A special kind of interferon variant has been described recently. The so-called "consensus interferons" are non-naturally occurring variants of IFN (U.S. Pat. No. 6,013,253). According to a preferred embodiment of the invention, the compounds of the invention are used in combination with a consensus interferon.

As used herein, human interferon consensus (IFN-con) shall mean a non-naturally-occurring polypeptide, which predominantly includes those amino acid residues that are common to a subset of IFN-alpha's representative of the majority of the naturally-occurring human leukocyte interferon subtype sequences and which includes, at one or more of those positions where there is no amino acid common to all subtypes, an amino acid which predominantly occurs at that position and in no event includes any amino acid residue which is not existent in that position in at least one naturally-occurring subtype. IFN-con encompasses but is not limited to the amino acid sequences designated IFN-con1, IFN-con2 and IFN-con3 which are disclosed in U.S. Pat. Nos. 4,695,623, 4,897,471 and 5,541,293. DNA sequences encoding IFN-con may be produced as described in the above-mentioned patents, or by other standard methods.

In a further preferred embodiment, the fused protein comprises an Ig fusion. The fusion may be direct, or via a short linker peptide which can be as short as 1 to 3 amino acid residues in length or longer, for example, 13 amino acid residues in length. Said linker may be a tripeptide of the sequence E-F-M (Glu-Phe-Met), for example, or a 13-amino acid linker sequence comprising Glu-Phe-Gly-Ala-Gly-Leu-Val-Leu-Gly-Gly-Gln-Phe-Met (SEQ ID NO: 1) introduced between the sequence of IFN and the immunoglobulin sequence. The resulting fusion protein may have improved properties, such as an extended residence time in body fluids (half-life), increased specific activity, increased expression level, or the purification of the fusion protein is facilitated.

In a further preferred embodiment, IFN is fused to the constant region of an Ig molecule. Preferably, it is fused to heavy chain regions, like the CH2 and CH3 domains of human IgG1, for example. Other isoforms of Ig molecules are also suitable for the generation of fusion proteins according to the present invention, such as isoforms $IgG_2$, $IgG_3$ or $IgG_4$, or other Ig classes, like IgM or IgA, for example. Fusion proteins may be monomeric or multimeric, hetero- or homomultimeric.

In a further preferred embodiment, the functional derivative comprises at least one moiety attached to one or more functional groups, which occur as one or more side chains on the amino acid residues. Preferably, the moiety is a polyethylene (PEG) moiety. PEGylation may be carried out by known methods, such as the ones described in WO99/55377, for example.

The dosage administered, as single or multiple doses, to an individual will vary depending upon a variety of factors, including pharmacokinetic properties, the route of administration, patient conditions and characteristics (sex, age, body weight, health, size), extent of symptoms, concurrent treatments, frequency of treatment and the effect desired.

The dosage of IFN-beta in the treatment of relapsing emitting MS according to the invention depends on the type of IFN-beta used.

In accordance with the present invention, where IFN is recombinant IFN-beta 1b produced in E. Coli, commercially available under the trademark Betaseron®, it may preferably be administered sub-cutaneously every second day at a dosage of about of 250 to 300 µg or 8 MIU to 9.6 MIU per person.

In accordance with the present invention, where IFN is recombinant IFN-beta1a, produced in Chinese Hamster Ovary cells (CHO cells), commercially available under the trademark Avonex®, it may preferably be administered intramuscularly once a week at a dosage of about of 30 µg to 33 µg or 6 MIU to 6.6 MIU per person.

In accordance with the present invention, when IFN is recombinant IFN-beta1a, produced in Chinese Hamster Ovary cells (CHO cells), commercially available under the trademark Rebif®, it may preferably be administered sub-cutaneously three times a week (TIW) at a dosage of 22 to 44 µg or 6 MIU to 12 MIU per person.

The administration of active ingredients in accordance with the present invention may be by intravenous, intramuscular or subcutaneous route. The preferred route of administration for IFN is the subcutaneous route. A further preferred route of administration is the intramuscular administration, which may e.g. be applied once a week.

IFN may also be administered daily or every other day, of less frequent. Preferably, IFN is administered one, twice or three times per week The term "stability" refers to the physical, chemical, and conformational stability of formulations of interferon of the present invention (including maintenance of biological potency). Instability of a protein formulation may be caused by chemical degradation or aggregation of the protein molecules to form higher order polymers, deglycosylation, modification of glycosylation, oxidation or any other structural modification that reduces at least one biological activity of an interferon polypeptide included in the present invention.

A "stable" solution or formulation, is one wherein the degree of degradation, modification, aggregation, loss of biological activity and the like, of proteins therein is acceptably controlled, and does not increase unacceptably with time. Preferably the formulation retains at least at or about 60%, more preferably at least at or about 70%, most preferably at least at or about 80% of the labelled interferon activity over a period of from 12 to 24 months. The stabilized HSA-free IFN compositions of the invention preferably have a shelf-life of at least about 6 months, 12 months, 18 months, more preferably at least 20 months, still more preferably at least about 22 months, most preferably at least about 24 months when stored at 2-8° C.

Methods for monitoring stability of the HSA-free IFN pharmaceutical compositions of the invention are available in the art, including those methods described in the examples disclosed herein. Thus, IFN aggregate formation during storage of a liquid pharmaceutical composition of the invention can be readily determined by measuring the change in soluble IFN in solution over time. Amount of soluble polypeptide in solution can be quantified by a number of analytical assays adapted to detection of IFN. Such assays include, for example, reverse phase (RP)-HPLC and UV absorption spectroscopy, as described in the Examples below.

Determination of both soluble and insoluble aggregates during storage in liquid formulations can be achieved, for example, using analytical ultracentrifugation as noted in the Examples below to distinguish between that portion of the soluble polypeptide that is present as soluble aggregates and that portion that is present in the nonaggregate, biologically active molecular form. In addition, velocity ultracentrifugation is able to detect both non-covalent and covalent oligomers both quantitatively and qualitatively. Likewise, a new size exclusion (SE)-HPLC method (described in the examples), herein referred to as "NEW SEC", is able to detect both covalent and non-covalent oligomers both quantitatively and qualitatively.

The expression "multi-dose use" is intended to include the use of a single vial, ampoule or cartridge of an interferon formulation for more than one injection, for example 2, 3, 4, 5, 6 or more injections. The injections are preferably made over a period of at least at or about 12 hours, 24 hours, 48 hours, etc., preferably up to a period of at or about 12 days. The injections may be spaced in time, for example, by a period of 6, 12, 24, 48 or 72 hours.

The term "amino acid" refers to an amino acid or a combination of amino acids, where any given amino acid is present either in its free base form or in its salt form. Where a combination of amino acids is used, all of the amino acids may be present in their free base forms, all may be present in their salt forms, or some may be present in their free base forms while others are present in their salt forms. Preferred amino acids to use in the present method or formulation of the present invention are those carrying a charged side chain, herein referred to as "charged side chain amino acid(s)", such as arginine, lysine, aspartic acid and glutamic acid. More preferably, the amino acid is lysine. Any stereoisomer (i.e., L, D, or DL isomer) of a particular amino acid, or combinations of these stereoisomers, may be used in the present method or formulation of the invention so long as the particular amino acid is present in its free base form or its salt form. Preferably, the L-stereoisomer is used. Analogues of these preferred amino acids may also be used in the present formulation of the invention. The term "amino acid analogue" refers to a derivative of the naturally occurring amino acid. Suitable arginine analogues include for example, aminoguanidine and N-monoethyl L-arginine. As with the preferred amino acids, the amino acids analogues are used in the present formulation in either their free base form or their salt form. Amino acids are herein also referred to as stabilizers.

The amino acid(s) used in the present formulation of the invention protects the therapeutically active polypeptide against various stresses thereby increasing or/and maintaining stability of the interferon-beta formulation. Herein, the term "stress" includes but is not limited to heat, freezing, pH, light, agitation, oxidation, dehydration, surfaces, shear, freeze/thawing, pressure, heavy metals, phenolic compounds, denaturants, etc. The term stress encompasses any factor that modulates (i.e. reduces, maintains or increases) the stability of the formulation containing interferon-beta. Increased and/or maintained stability with addition of an amino acid occurs in a concentration dependent manner. That is, increasing concentrations of amino acid lead to increased and/or maintained stability of the formulation containing interferon-beta of the present invention when that formulation containing interferon-beta normally exhibits aggregate or oligomer formation in the absence of the amino acid. Determination of the amount of a particular amino acid to be used in the present formulation of the invention, in order to decrease oligomer or aggregate formation and thereby increasing monomeric protein stability, can readily be determined without undue experiment using methods generally known to one of skill in the art.

The term "buffer" or "physiologically-acceptable buffer" refers to solutions of compounds that are known to be safe for pharmaceutical or veterinary use in formulations and that have the effect of maintaining or controlling the pH of the formulation in the pH range desired for the formulation. Acceptable buffers for controlling pH at a moderately acidic pH to a moderately basic pH include, but are not limited to, such compounds as phosphate, acetate, citrate, arginine, TRIS, and histidine. "TRIS" refers to 2-amino-2-hydroxymethyl-1,3,-propanediol, and to any pharmacologically acceptable salt thereof. Preferable buffers are acetate buffers with saline or an acceptable salt.

An "isotonicity agent" is a compound that is physiologically tolerated and imparts a suitable tonicity to a formulation to prevent the net flow of water across cell membranes that are in contact with the formulation. Compounds such as glycerin, are commonly used for such purposes at known concentrations. Other suitable isotonicity agents include, but are not limited to, mannitol, amino acids or proteins (e.g. glycine or albumin), salts (e.g. sodium chloride), and sugars (e.g. dextrose, mannitol, sucrose and lactose).

The term "antioxidant" refers to a compound that prevents oxygen or oxygen-derived free radicals from interacting with other substances. Antioxidants are among a number of excipients commonly added to pharmaceutical systems to enhance physical and chemical stability. Antioxidants are added to minimize or retard oxidative processes that occur with some drugs or excipients upon exposure to oxygen or in the presence of free radicals. These processes can often be catalyzed by light, temperature, hydrogen on concentration, presence of trace metals or peroxides. Sulfites, bisufites, thiourea, methionine, salts of ethylenediaminetetraacetic acid (EDTA), butylated hydroxytoluene (BHT), and butylated hydroxy anisole (BHA) are frequently used as antioxidants in drugs. Sodium EDTA has been found to enhance the activity of antioxidants by chelating metallic ions that would otherwise catalyze the oxidation reaction. Most preferred antioxidant is methionine. Antioxidants are herein also referred to as stabilizers.

Methionine can be present either in its free base form or in its salt form. Any stereoisomer (i.e., L, D, or DL isomer) of methionine may be used in the present method or formulation of the invention so long as methionine is present in its free base form or its salt form. Preferably, the L-stereoisomer is used. Analogues of methionine may also be used in the present formulation of the invention. The term "methionine analogue" refers to a derivative of the naturally occurring methionine. The methionine analogues can also be used in the present formulation in either their free base form or their salt form.

Increased and/or maintained stability with addition of antioxidants (e.g. methionine) occurs in a concentration dependent manner. That is, increasing concentrations of antioxidants lead to increased and/or maintained stability of the formulation containing interferon-beta of the present invention when that formulation containing interferon-beta normally exhibits oxidation or aggregate/oligomer formation in the absence of the antioxidant. Determination of the amount of an oxidant (e.g. methionine) to be used in the present formulation of the invention, in order to decrease oxidation or oligomer/aggregate formation, can readily be determined without undue experiment using methods generally known to one of skill in the art.

The term "bacteriostatic" refers to a compound or compositions added to a formulation to act as an anti-bacterial agent. Examples of bacteriostatics include phenol, m-cresol, p-cresol, o-cresol, chlorocresol, benzyl alcohol, alkylparaben (methyl, ethyl, propyl, butyl and the like), benzalkonium chloride, benzethonium chloride, sodium dehydroacetate and thimerosal. Preferably the bacteriostatic agent is benzyl alcohol.

The term "surfactant" refers to a soluble compound that reduces the surface tension of liquids, or reduces interfacial tension between two liquids or a liquid and a solid, the surface tension being the force acting on the surface of a liquid, tending to minimize the area of the surface. Surfactants have sometimes been used in pharmaceutical formulations, including delivery of low molecular mass drugs and polypeptides, in order to modify the absorption of the drug or its delivery to the target tissues. Well known surfactants include polysorbates (Polyoxyethylene derivatives; Tween) as well as Pluronic.

According to a preferred embodiment of the invention, it has been found that by formulating interferon with a surfactant selected from PLURONIC F77, PLURONIC F87, PLURONIC F88 and PLURONIC F68, particularly preferably PLURONIC F68 (BASF, PLURONIC F68 is also known as Poloxamer 188), a stable formulation is obtained that minimise the loss of active principle caused by adsorption on the surfaces of the vial and/or delivery device (e.g. syringe, pump, catheter, etc.). It has also been found that by formulating interferon with a surfactant selected from PLURONIC F77, PLURONIC F87, PLURONIC F88 and PLURONIC F68, particularly preferably PLURONIC F68 (BASF, PLURONIC F68 is also known as Poloxamer 188), a stable formulation is obtained, which is more resistant to oxidation and to formation of proteins aggregates.

The Pluronic surfactants are block copolymers of ethylene oxide (EO) and propylene oxide (PO). The propylene oxide block (PO) is sandwiched between two ethylene oxide (EO) blocks.

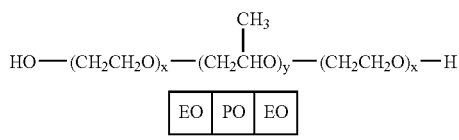

Pluronic surfactants are synthesized in a two-step process:

1. A hydrophobe of the desired molecular weight is created by the controlled addition of propylene oxide to the two hydroxyl groups of propylene glycol; and 2. Ethylene oxide is added to sandwich the hydrophobe between hydrophilic groups.

In PLURONIC F77, the percentage of polyoxyethylene (hydrophile) is 70%, and the molecular weight of the hydrophobe (polyoxypropylene) is approximately 2,306 Da.

In Pluronic F87, the percentage of polyoxyethylene (hydrophile) is 70%, and the molecular weight of the hydrophobe (polyoxypropylene) is approximately 2,644 Da.

In Pluronic F88, the percentage of polyoxyethylene (hydrophile) is 80%, and the molecular weight of the hydrophobe (polyoxypropylene) is approximately 2,644 Da.

In Pluronic F68, the percentage of polyoxyethylene (hydrophile) is 80%, and the molecular weight of the hydrophobe (polyoxypropylene) is approximately 1,967 Da.

Typical properties of Pluronic F77 are listed below:
Average Molecular Weight: 6600;
Melt/pour point: 48° C.;
Physical Form@20° C.: solid;
Viscosity (Brookfield) cps: 480 [liquids at 25° C., pastes at 60° C. and solids at 77° C.];
Surface tension, dynes/cm@25° C.;
   0.1% Conc.: 47.0
   0.01% Conc.: 49.3
   0.001% Conc.: 52.8
Interfacial tension, dynes/cm@25° C. vs. Nujol;
   0.1% Conc.: 17.7
   0.01% Conc.: 20.8
   0.01% Conc.: 25.5
Draves Wetting, Seconds 25° C.
   1.0% Conc.: >360
   0.1% Conc.: >360
Foam Height
   Ross Miles, 0.1%, mm@50° C.: 100
   Ross Miles, 0.1%, mm@26° C.: 47
   Dynamic, 0.1%, mm@400 ml/min: >600
Cloud point in aqueous solution, ° C.
   1% Conc.: >100
   10% Conc.: >100
HLB (hydrophile-lipophile balance): 25
Typical properties of Pluronic F87 are listed below:
Average Molecular Weight: 7700;
Melt/pour point: 49° C.;
Physical Form@20° C.: solid;
Viscosity (Brookfield) cps: 700 [liquids at 25° C., pastes at 60° C. and solids at 77° C.];
Surface tension, dynes/cm@25° C.;
   0.1% Conc.: 44.0
   0.01% Conc.: 47.0
   0.001% Conc.: 50.2
Interfacial tension, dynes/cm@25° C. vs Nujol;
   0.1% Conc.: 17.4
   0.01% Conc.: 20.3
   0.01% Conc.: 23.3
Draves Wetting, Seconds 25° C.
   1.0% Conc.: >360
   0.1% Conc.: >360
Foam Height
   Ross Miles, 0.1%, mm@50° C.: 80
   Ross Miles, 0.1%, mm@26° C.: 37
   Dynamic, 0.1%, mm@400 ml/min: >600
Cloud point in aqueous solution, ° C.
   1% Conc.: >100
   10% Conc.: >100
HLB (hydrophile-lipophile balance): 24
Typical properties of Pluronic F88 are listed below:
Average Molecular Weight: 11400;
Melt/pour point: 54° C.;
Physical Form@20° C.: solid;
Viscosity (Brookfield) cps: 2300 [liquids at 25° C., pastes at 60° C. and solids at 77° C.];
Surface tension, dynes/cm@25° C.;
   0.1% Conc.: 48.5
   0.01% Conc.: 52.6
   0.001% Conc.: 55.7
Interfacial tension, dynes/cm@25° C. vs Nujol;
   0.1% Conc.: 20.5
   0.01% Conc.: 23.3
   0.01% Conc.: 27.0
Draves Wetting, Seconds 25° C.
   1.0% Conc.: >360
   0.1% Conc.: >360
Foam Height
   Ross Miles, 0.1%, mm@50° C.: 80
   Ross Miles, 0.1%, mm@26° C.: 37
   Dynamic, 0.1%, mm@400 ml/min: >600
Cloud point in aqueous solution, ° C.
   1% Conc.: >100
   10% Conc.: >100
HLB (hydrophile-lipophile balance): 28
Typical properties of Pluronic F68 are listed below:
Average Molecular Weight: 8400;
Melt/pour point: 52° C.;
Physical Form@20° C.: solid;
Viscosity (Brookfield) cps: 1000 [liquids at 25° C., pastes at 60° C. and solids at 77° C.];
Surface tension, dynes/cm@25° C.;
   0.1% Conc.: 50.3
   0.01% Conc.: 51.2
   0.001% Conc.: 53.6

Interfacial tension, dynes/cm@25° C. vs Nujol;
  0.1% Conc.: 19.8
  0.01% Conc.: 24.0
  0.01% Conc.: 26.0
Draves Wetting, Seconds 25° C.
  1.0% Conc.: >360
  0.1% Conc.: >360
Foam Height
  Ross Miles, 0.1%, mm@50° C.: 35
  Ross Miles, 0.1%, mm@26° C.: 40
  Dynamic, 0.1%, mm@400 ml/min: >600
Cloud point in aqueous solution, ° C.
  1% Conc.: >100
  10% Conc.: >100
HLB (hydrophile-lipophile balance): 29

Other polymers having properties similar to those listed above may also be used in the formulations of the invention. The preferred surfactant is Pluronic F68, and surfactants having similar properties.

Pluronic, particularly Pluronic F68, is preferably present at a concentration that is sufficient to maintain interferon stability over the desired storage period (for example 12 to 24 months), and also at a concentration that is sufficient to prevent protein losses due to adsorption on surfaces, such as the vial, ampoule or cartridge or the syringe.

Preferably the concentration of Pluronic, particularly Pluronic F68, in liquid formulations is at or about 0.01 mg/ml to at or about 10 mg/ml, more preferably at or about 0.05 mg/ml to at or about 5 mg/ml, more particularly preferably at or about 0.1 mg/ml to at or about 2 mg/ml, most preferably at or about 0.5 mg/ml.

Preferably the concentration of IFN-beta1a in the formulation is at or about 10 μg/ml to at or about 800 μg/ml, more preferably at or about 20 μg/ml to at or about 500 μg/ml, more particularly preferably at or about 30 to at or about 300 μg/ml, most preferably at or about 22, 44, 88 or 264 μg/ml.

Preferably the formulations of the present invention have a pH between at or about 3.5 and at or about 5.5, more preferably at or about 4.7. A preferred buffer is acetate, with preferred counterions being sodium or potassium ions. Acetate saline buffers are well known in the art. Buffer concentrations in total solution can vary between at or about 5 mM, 9.5 mM, 10 mM, 50 mM, 100 mM, 150 mM, 200 mM, 250 mM, and 500 mM. Preferably the buffer concentration is at or about 10 mM. Particularly preferred is a buffer 10 mM in acetate ions with a pH of 4.7±0.2.

Preferably, in the composition of the invention, the antioxidant, for example methionine, is present at a concentration at or about 0.01 to at or about 5.0 mg/ml, more preferably at or about 0.05 to at or about 0.3 mg/ml, most preferably at or about 0.12 mg/ml.

Preferably, in the composition of the invention, the amino acid, for example lysine, is present at a concentration at or about 1 to at or about 100 mg/ml, more preferably at or about 10 to at or about 50 mg/ml, most preferably at or about 27.3 mg/ml.

The invention includes liquid formulations. The preferred solvent is water for injection.

Liquid formulations may be mono-dose or multi-dose. Those liquid interferon formulations of the invention that are intended for multi-dose use preferably comprise a bacteriostatic, such as phenol, m-cresol, p-cresol, o-cresol, chlorocresol, benzyl alcohol, alkylparaben (methyl, ethyl, propyl, butyl and the like), benzalkonium chloride, benzethonium chloride, sodium dehydroacetate and thimerosal. Particularly preferred are phenol, benzyl alcohol and m-cresol, more preferred is benzyl alcohol. The bacteriostatic agent is used in an amount that will yield a concentration that is effective to maintain the formulation essentially bacteria free (suitable for injection) over the multi-dose injection period, which may be at or about 12 or 24 hours to at or about 12 days, preferably at or about 6 to at or about 12 days. The bacteriostatic is preferably present in a concentration of at or about 0.1% (mass bacteriostatic/mass of solvent) to at or about 2.0%, more preferably at or about 0.2% to at or about 1.0%. In the case of benzyl alcohol, particularly preferred are concentrations of 0.2 or 0.3%).

However, the use of a preservative, e.g. benzyl alcohol, is not limited to multi-dose formulations, but may also be added in mono-dose formulations. One embodiment of the present invention consists in single dose formulations containing benzyl alcohol.

In a further embodiment of the formulations according to the present invention the interferon beta is in at least about 96% or at least about 98% in its monomer form (less than 4, more preferably less than 2% of aggregates) at room temperature or at 2-8° C., as measured by sedimentation velocity analysis described below.

A preferred formulation consists of interferon-beta 1a, benzyl alcohol, lysine, methionine, Pluronic F-68 and an aqueous acetate buffer, preferably to adjust the pH to 3.7 to 4.7.

The range of interferon in the formulations of the invention includes amounts yielding upon reconstitution, concentrations at or about 1.0 μg/ml to at or about 50 mg/ml, although lower and higher concentrations are operable and are dependent on the intended delivery vehicle, e.g., solution formulations will differ from transdermal patch, pulmonary, transmucosal, or osmotic or micro pump methods. The interferon concentration is preferably at or about 5.0 μg/ml to at or about 2 mg/ml, more preferably at or about 10 μg/ml to at or about 1 mg/ml, most preferably at or about 30 μg/ml to at or about 100 μg/ml.

Preferably the formulations of the invention retain at least at or about 60%, more preferably at least at or about 70%, most preferably at least at or about 80% of the interferon activity at the time of packaging over a period of 24 months.

In a further preferred embodiment, the invention provides a method for manufacturing a liquid pharmaceutical composition as described before.

In yet another preferred embodiment, the invention provides a method for manufacturing a packaged pharmaceutical composition comprising placing a solution comprising the active ingredient and the excipients as described before.

In yet another preferred embodiment, the invention provides an article of manufacture for human pharmaceutical use, comprising a vial comprising the pharmaceutical compositions as described before, and written material stating that such solution may be held over a period of at or about twenty-four hours or greater after the first use. Preferably the written material states that the solution may be held up to at or about 12 days.

After the first use of a multi-dose formulation it may be kept and used for at least at or about 24 hours, preferably at least at or about 4, 5 or 6 days, more preferably for up to 12 days. After the first use the formulation is preferably stored at below room temperature (i.e. below at or about 25° C.), more preferably below at or about 10° C., more preferably at or about 2-8° C., most preferably at or about 4-6° C.

The formulations of the present invention can be prepared by a process which comprises adding the calculated amounts of the excipients to the buffered solution and then adding the interferon.

The resulting solution is then placed in vials, ampoules or cartridges. Variations of this process would be recognized by one of ordinary skill in the art. For example, the order the components are added, whether additional additives are used, the temperature and pH at which the formulation is prepared, are all factors that may be optimised for the concentration and means of administration used.

In case of a multi-dose use formulation, the bacteriostatic agent may be added to the solution containing the active ingredient (interferon) or alternatively may be kept in a separate vial or cartridge and subsequently mixed to the solution containing the active ingredient at the moment of use.

The formulations of the invention can be administered using recognized devices. Examples comprising these single vial systems include auto-injector or pen-injector devices for delivery of a solution such as REBIJECT.

The products presently claimed include packaging material. The packaging material provides, in addition to the information required by the regulatory agencies, the conditions under which the product may be used. The packaging material of the present invention provides instructions to the patient, if needed, to prepare the final solution and to use such final solution over a period of twenty-four hours or greater for the two vial, wet/dry, product. For the single vial, solution product, the label indicates that such solution may be used over a period of twenty-four hours or greater. The presently claimed products are useful for human pharmaceutical product use.

The stable preserved formulations may be provided to patients as clear solutions. The solution may be for single use or it may be reused multiple times and may suffice for a single or multiple cycles of patient treatment and thus provides a more convenient treatment regimen than currently available.

The interferon in either the stable or preserved formulations or solutions described herein, may be administered to a patient in accordance with the present invention via a variety of delivery methods including SC or IM injection; transdermal, pulmonary, transmucosal, implant, osmotic pump, cartridge, micro pump, oral, or other means appreciated by the skilled artisan, as well-known in the art.

The term "vial" refers broadly to a reservoir suitable for retaining interferon in solid or liquid form in a contained sterile state. Examples of a vial as used herein include ampoules, cartridges, blister packages, or other such reservoir suitable for delivery of the interferon to the patient via syringe, pump (including osmotic), catheter, transdermal patch, pulmonary or transmucosal spray. Vials suitable for packaging products for parenteral, pulmonary, transmucosal, or transdermal administration are well known and recognized in the art.

The term "treatment" within the context of this invention refers to any beneficial effect on progression of disease, including attenuation, reduction, decrease or diminishing of the pathological development after onset of disease.

Pharmaceutical compositions of the invention comprising IFN or an isoform, mutein, fused protein, functional derivative, active fraction or salt are useful in the diagnosis, prevention, and treatment (local or systemic) of clinical indications responsive to therapy with this polypeptide. Such clinical indications include, for example, disorders or diseases of the central nervous system (CNS), brain, and/or spinal cord, including multiple sclerosis; autoimmune diseases, including rheumatoid arthritis, psoriasis, Crohn's disease; and cancers, including breast, prostate, bladder, kidney and colon cancers.

All references cited herein, including journal articles or abstracts, published or unpublished U.S. or foreign patent application, issued U.S. or foreign patents or any other references, are entirely incorporated by reference herein, including all data, tables, figures and text presented in the cited references. Additionally, the entire contents of the references cited within the references cited herein are also entirely incorporated by reference.

Reference to known method steps, conventional methods steps, known methods or conventional methods is not any way an admission that any aspect, description or embodiment of the present invention is disclosed, taught or suggested in the relevant art.

The foregoing description of the specific embodiments will so fully reveal the general nature of the invention that others can, by applying knowledge within the skill of the art (including the contents of the references cited herein), readily modify and/or adapt for various application such specific embodiments, without undue experimentation, without departing from the general concept of the present invention. Therefore, such adaptations and modifications are intended to be within the meaning of a range of equivalents of the disclosed embodiments, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance presented herein, in combination with the knowledge of one of ordinary skill in the art.

EXAMPLES

Example 1

Analytical Methods

Size exclusion (SE)-HPLC, herein also referred as "new SE-HPLC" or "NEW SEC", and velocity ultracentrifugation (AUC) were used for the measurement of aggregates' and oligomers' levels of recombinant human interferon-beta 1a (r-h IFN-beta 1a or r-hβIFN-1a). The SE-HPLC and AUC methods presented below are able to detect both covalent and non-covalent oligomers both quantitatively and qualitatively.

a. SE-HPLC—Purity Test

The detection of the total aggregates content is performed on a TSK G2000SWXL column (TosoHaas) or a BioSuite (Waters); the elution is performed in isocratic mode at 0.5 mL/min using 50 mM sodium acetate buffer, 50 mM NaCl pH 3.8; the wavelength is set at 215 nm. The runtime is 30 min.

Samples at 88 mcg/mL are analysed as it is by injecting 100 µl.

b. Sedimentation Velocity Analysis—AUC

1. Method Description

Samples are loaded into cells with 2-channel charcoal-epon centrepieces with 12 mm optical pathlength. The centerpieces and sapphire windows are cleaned with detergent and then soaked in water to try to have the cleanest possible surfaces. The corresponding placebo is loaded in the reference channel (the instrument functions like a dual-beam spectrophotometer). Those loaded cells are then placed into an AN-50Ti analytical rotor, loaded into a Beckman Optima XL-I analytical centrifuge, and brought to 20° C. The rotor is then brought to 3000 rpm and the samples are scanned (at 280 nm, the absorbance peak) to confirm proper cell loading. The rotor is then brought to the final run speed of 50000 rpm. 50 scans for each sample are recorded at this rotor speed.

Data are analysed using the c(s) method developed by Peter Schuck at the N.I.H. and implemented in his analysis program SEDFIT (version 8.7; Schuck, P. (2000). Size-distribution analysis of macromolecules by sedimentation velocity ultracentrifugation and Lamm equation modelling. *Biophys. J.* 78, 1606-1619).

In this approach many raw data are directly fitted to derive the distribution of sedimentation coefficients, while modelling the influence of diffusion on the data in order to enhance the resolution. The method works by assigning a diffusion coefficient to each value of sedimentation coefficient based on an assumption that all species have the same overall hydrodynamic shape (with shape defined by the frictional coefficient ratio relative to that for a sphere, $f/f_0$). The $f/f_0$ values are then varied to find the best overall fit of the data for each sample. The distributions are calculated using 0.51 maximum-entropy smoothing.

2. Analytical Parameters

| | |
|---|---|
| Rotor type | 8-holes rotor |
| Rotor speed | 50k rpm |
| Centerpieces | charcoal epon |
| Channel length | 12 mm |
| Temperature during the AUC run | 20° C. |
| Detection wavelength | 280 nm |
| Sample volume | 432 mcl |
| Reference volume | 442 mcl |

3. Equipment and Software

Analytical Ultracentrifuge Model XL-I (Beckman Coulter)
SEDFIT ver 8.70b Software (Peter Schuck—National Institutes of Health)
Origin ver 6.03 Software (Beckman Coulter)
Proteome Lab XL-A/XL-I ver 5.0 Software (Beckman Coulter)

c. IFN-β-1a Quantitation by RP-HPLC—QUANT-HPLC

The reverse phase method described below enables the quantification of IFN-β-1-a in samples.

The quantification of the protein is performed on a C4, Wide-Pore Butyl 5 μm, 4.6×250 mm column (Baker); the wavelength is set at 214 nm and the elution is performed at 1 mL/min using the following mobile phase and gradient:

A=water/trifluoroacetic acid 0.1%-B=acetonitrile/trifluoroacetic acid 0.1%-C=acetonitrile Samples are analysed by injecting 50 μL of the sample as it is (88 mcg/mL samples).

TABLE 4

| Time (min.) | % Eluent A | % Eluent B | % Eluent C |
|---|---|---|---|
| 0 | 70 | 30 | 0 |
| 5.0 | 70 | 30 | 0 |
| 6.0 | 58 | 42 | 0 |
| 15.0 | 57 | 43 | 0 |
| 30.0 | 46 | 54 | 0 |
| 35.0 | 45 | 55 | 0 |
| 40.0 | 40 | 60 | 0 |
| 40.1 | 20 | 80 | 0 |
| 45.0 | 20 | 80 | 0 |
| 45.1 | 0 | 0 | 100 |
| 50.0 | 0 | 0 | 100 |
| 50.1 | 70 | 30 | 0 |
| 65.0 | 70 | 30 | 0 |

Runtime = 65 min

The quantification of the samples is performed versus a standard curve in the range 0.0125 mg/mL-0.2 mg/mL prepared by a reference standard material.

d. Purity by Reverse Phase (RP)-HPLC—DEG/OX

The reverse phase method described below enables the detection of IFN-β-1a oxidized forms, which elute differently from the intact molecule.

The quantification of the oxidised forms is performed on a C4, Supelcosil LC-304 column (Supelco) thermostated at 40° C.; the wavelength is set at 208 nm and the elution is performed at 1 mL/min using the following mobile phase and gradient:

A=water 60%/acetonitrile 40%/Heptafluorobutirric acid 0.14%-B=water 20%/Acetonitrile 80%/Heptafluorobutirric acid 0.14%-C=water 20%/Acetonitrile 80%/Trifluroacetic acid 0.1%

Gradient:

TABLE 5

| | | | | |
|---|---|---|---|---|
| 0' | 70% A | 30% B | 0% C | |
| 5' | 70% A | 30% B | 0% C | |
| 58' | 62% A | 38% B | 0% C | Curve 6 |
| 63' | 0% A | 100% B | 0% C | Curve 1 |
| 68' | 0% A | 0% B | 100% C | Curve 1 |
| 69' | 70% A | 30% B | 0% C | Curve 6 |

Runtime: 96 minutes (70 min + 26 min equilibration)

Samples are analysed as it is by injecting 200 μL (88 mcg/mL samples).

e. Cytopathic Effect Inhibition Bioassay—CPE

Biopotency (Antiviral Activity)

The antiviral activity of IFN-β-1a is measured by the cytopathic effect (CPE) inhibition bioassay.

The biological activity is measured by an antiviral assay based on the IFN-β induced protection of cells (WISH cells-human amniotic tissue) against the cytopathic effect of a virus (Vesicular Stomatitis Virus).

The principle of the bioassay for interferon lies on the fact that a number of viruses such as Vesicular Stomatitis Virus (VSV) cause cell death that can be visualized by vital staining.

The cytopathic effect can then be used to quantify cell protection by interferon.

The assay is performed by the indirect measure of cell death, which is assessed by the amounts of dye tetrazolium salt MTT (Dimethylthiotetrazolium) taken up by living cells.

The method makes use of automatic spectrophotometric determination of the percent of protected cells and of a three point parallel line assay for the statistical evaluation of the titer.

Procedure:

The assay is performed in microtiter plates.
a. 50 μl of cell culture medium (MEM/5% FBS) are added to each well.
b. 100 μl of IFN-β-1a sample or standard solution (60-100 IU hIFN-β/ml) are added to the wells and three 1:1.5 step dilutions are performed from row to row in the plates.
c. A 50 μl suspension of WISH cells (0.78-0.82×10$^6$ cells/ml) is added to each well and the plates are incubated at 37° C. for 18-20 hours in a 5% $CO_2$ humidified incubator.
d. A VSV suspension is added to each well except the cell control wells, filled with MEM/2.5% FBS.
e. The plates are incubated for 24 hours in a 5% $CO_2$ humidified incubator at 37° C.
f. After having verified by an inverted microscope that
 (1) at least 80% of cell damage is achieved in the VSV control row and
 (2) the percentage mean values of protection in presence of the IFN-β standard fall in the range of 84% for the non diluted standard, 45% for the 1:1.5 dilution, and 27% for the 1:3 dilution the cultures are stained with the specific dye MTT.
g. The intensity of the coloration is determined by automatic spectrophotometric reading at 592 nm.
h. To quantitate the IFN-β-1a activity, the OD readings are then analyzed by a computer program (Colombo Software).

Example 2

Stabilization of HSA-Free Interferon Beta-1a Formulations

The following experiment was conducted to verify the protective effect exerted by a formulation comprising an amino acid (i.e. lysine) and an antioxidant (i.e. methionine) on storage of a r-h IFN-beta 1a formulation at various temperatures (2-8° C., 25° C. and 40° C.). The following analytical tests and methods were used during the development (see example 1):

- biological activity (in vitro bioassay)
- assay (RP-HPLC method)
- oxidation products (Deg-ox method)
- dimers/aggregates (NEW SEC-HPLC and AUC, both methods are able to detect covalent and non-covalent oligomers)
- quantitative RP-HPLC method (Quant-HPLC)
- pH (potentiometric method)

Results are indicated in tables 6 to 8.

1. Procedure:
   a. The formulation was manufactured using a bulk stored/shipped at 2-8° C. The concentration of r-h IFN-beta 1a in the bulk was about 0.5 mg/mL.
   a. The formulation, comprising lysine (as indicated in point 2.), was manufactured by diluting the drug substance in a vehicle thus reaching the final composition (r-h IFN-beta 1a concentration 88 mcg/mL).
   b. The compounded solution was then aseptically filtered through a 0.2 micron nylon membrane and collected into a sterile container; the syringes were then filled with 0.5 mL using a filling machine.
   c. The sample was then stored in thermostatic cabinets at 2-8° C., 25° C. and 40° C. and tested according to a stability plan using various methods/tests up to about 2 months of storage (1-3 weeks for samples stored at 40° C.).

2. Composition of the Formulation:
   a. 0.088 mg/mL r-h interferon-beta 1a
   b. 27.3 mg/mL L-lysine monohydrochloride (code 1.05701, Merck)
   c. 0.12 mg/mL L-Methionine (1.05707, Merck)
   d. 0.5 mg/mL Pluronic F-68 (Lutrol F 68 DAC, USP/NF, Basf), 5163315
   e. 10 mM sodium acetate pH 4.7.

3. Results:

TABLE 6

| | Storage at 2-8° C. 2-8° C. | | | |
|---|---|---|---|---|
| | T = 0 | 4 w | 6 w | 8 w |
| Quant-HPLC (mcg/syr) | 39.0 | 38.2 | 39.8 | 39.2 |
| Deg-ox HPLC (% oxidized) | 1.3 | 1.5 | 1.5 | 1.5 |
| AUC (% monomer) | 98.7 | — | 98.8 | — |
| New-SEC (% monomer) | 100.0 | 100.0 | 100.0 | 100.0 |
| PH | 4.7 | 4.7 | — | 4.7 |
| Bioassay (MIU/mL) | 24.1 | 24.6 | — | — |
| Osmolarity (OSM/kg) | 0.303 | — | — | — |

TABLE 7

| | Storage at 25° C. 25° C. | | | | |
|---|---|---|---|---|---|
| | T = 0 | 2 w | 4 w | 6 w | 8 w |
| Quant-HPLC (mcg/syr) | 39.0 | 42.8 | 38.0 | 39.4 | 37.8 |
| Deg-ox HPLC (% oxidized) | 1.3 | 1.5 | 1.4 | 2.3 | 2.3 |
| AUC (% monomer) | 98.7 | 99.0 | — | 98.2 | — |
| New-SEC (% monomer) | 100.0 | 100.0 | 100.0 | 100.0 | 100.0 |
| PH | 4.7 | 4.7 | 4.7 | — | 4.7 |

TABLE 7-continued

| | Storage at 25° C. 25° C. | | | | |
|---|---|---|---|---|---|
| | T = 0 | 2 w | 4 w | 6 w | 8 w |
| Bioassay (MIU/mL) | 24.1 | — | 24.0 | — | — |

TABLE 8

| | Storage at 40° C. 40° C. | | |
|---|---|---|---|
| | T = 0 | 1 w | 3 w |
| Quant-HPLC (mcg/syr) | 39.0 | 37.8 | 34.9 |
| Deg-ox HPLC (% oxidized) | 1.3 | 1.9 | 3.4 |
| AUC (% monomer) | 98.7 | 99.6 | — |
| New-SEC (% monomer) | 100.0 | 100.0 | 100.0 |
| pH | 4.7 | 4.7 | 4.6 |

4. Conclusions:

Storage studies show that a formulation or composition comprising lysine, methionine and pluronic F-68 remains very stable at 2-8° C. as well as at 25° C. up to 8 weeks. They remain stable at 40° C. up to 3 weeks in terms of level of monomer percentage (monomer percentage is always higher than 98%). Two different methods confirmed these results (AUC and NEW-SE-HPLC). Thus, the formulation of the present invention preferably comprises a combination of an amino acid and an antioxidant. Preferably, a surfactant is further added to the composition.

Preferably, the amino acid is lysine and the antioxidant is methionine. Preferably, the surfactant is selected from tween (e.g. tween 20), PLURONIC F77, PLURONIC F87, PLURONIC F88 and PLURONIC F68. More preferably, the surfactant is PLURONIC F68.

Preferably, the formulation is set at a range of pH 3.5 to 5.5. More preferably, the formulation is set at a pH of 4.7.

Preferably, lysine is present at a concentration of about 1 mg/ml to about 100 mg/ml. More preferably, lysine is present at a concentration of about 27.3 mg/ml. Preferably, the surfactant is present at a concentration of about 0.01 mg/ml to about 10 mg/ml. More preferably, the surfactant is present at a concentration of about 0.5 mg/ml. Preferably, the antioxidant is present at a concentration of about 0.01 to about 5.0 mg/ml. More preferably, the antioxidant is present at a concentration of about 0.12 mg/ml. Preferably, the interferon is present at a concentration of about 10 μg/ml to about 800 μg/ml. More preferably, the interferon is present at a concentration of about 88 μg/ml.

REFERENCES

1. Derynk R. et al., Nature 1980; 285, 542-547.
2. Familletti, P. C., Rubinstein, S., and Pestka, S. 1981 "A Convenient and Rapid Cytopathic Effect Inhibition Assay for Interferon," in Methods in Enzymology, Vol. 78 (S. Pestka, ed.), Academic Press, New York, 387-394;
3. Mark D. F. et al., Proc. Natl. Acad. Sci. U.S.A., 81 (18) 5662-5666 (1984).
4. Pestka, S. (1986) "Interferon Standards and General Abbreviations, in Methods in Enzymology (S. Pestka, ed.), Academic Press, New York 119, 14-23.
5. Rubinstein, S., Familletti, P. C., and Pestka, S. Convenient Assay for Interferons. J. Virol 1981; 37, 755-758.
6. Shepard H. M. et al., Nature 1981; 294, 563-565.

The invention claimed is:

1. A composition comprising:
   a) about 88 μg/ml interferon-beta 1a
   b) about 27.3 mg/ml lysine;
   c) about 0.12 mg/ml methionine;
   d) about 0.5 mg/ml poloxomer 188; and
   e) an aqueous acetate buffer at a pH of 3.5 to 5.5.

2. A composition comprising interferon-beta 1a, lysine, methionine and poloxomer 188 in an aqueous acetate buffer having a pH of about 3.4 to 5.5, said composition containing interferon-beta 1a, lysine, methionine and poloxomer 188 at a ratio of interferon-beta 1a:lysine:methionine:poloxomer 188 of about: 1:310:1.4:5.7.

* * * * *

UNITED STATES PATENT AND TRADEMARK OFFICE
CERTIFICATE OF CORRECTION

PATENT NO. : 7,731,948 B2
APPLICATION NO. : 11/597987
DATED : November 30, 2006
INVENTOR(S) : Fabrizio Samaritani and Alessandra Del Rio It is certified that error appears in the above-identified patent and that said Letters Patent is hereby corrected as shown below:

Column 8,
Lines 7-8, "relapsing emitting" should read --relapsing-remitting--.

Column 11,
Lines 11-12, "that minimise" should read --that minimises--.

Column 16,
Line 21, "referred as" should read --referred to as--.

Column 18,
Line 39, "IU h1FN-β/ml)" should read --IU hIFN-β/ml)--.

Signed and Sealed this

Fifth Day of October, 2010

David J. Kappos
*Director of the United States Patent and Trademark Office*

```
                              SEQUENCE LISTING

<160> NUMBER OF SEQ ID NOS: 1

<210> SEQ ID NO 1
<211> LENGTH: 13
<212> TYPE: PRT
<213> ORGANISM: Artificial sequence
<220> FEATURE:
<223> OTHER INFORMATION: amino acid linker sequence

<400> SEQUENCE: 1

Glu Phe Gly Ala Gly Leu Val Leu Gly Gly Gln Phe Met
1               5                   10
```